US00PP24556P2

(12) United States Plant Patent
van Elderen

(10) Patent No.: US PP24,556 P2
(45) Date of Patent: Jun. 17, 2014

(54) *DISPORUM* PLANT NAMED 'MOONLIGHT'

(50) Latin Name: *Disporum cantoniense*
Varietal Denomination: Moonlight

(76) Inventor: Reinier van Elderen, Lijnden (NL)

( * ) Notice: Subject to any disclaimer, the term of this patent is extended or adjusted under 35 U.S.C. 154(b) by 295 days.

(21) Appl. No.: 13/385,266

(22) Filed: Feb. 10, 2012

(51) Int. Cl.
*A01H 5/00* (2006.01)

(52) U.S. Cl.
USPC ..... Plt./263.1

(58) Field of Classification Search
USPC ..... Plt./263.1, 226
See application file for complete search history.

*Primary Examiner* — Kent L Bell
(74) *Attorney, Agent, or Firm* — Penny J. Aguirre

(57) ABSTRACT

A new cultivar of *Disporum* named 'Moonlight', that is characterized by its arching stems and its variegated foliage that is green with silvery white variegation palmately radiating from the base of the leaf blade with the white variegation area becoming heavily suffused with a purple-pink coloration in fall when temperatures cool.

3 Drawing Sheets

Genus and species: *Disporum cantoniense.*
Cultivar: 'Moonlight'.

BACKGROUND OF THE INVENTION

The present invention relates to a new and distinct cultivar of *Disporum cantoniense* and will be referred to hereafter by its cultivar name, 'Moonlight'. 'Moonlight' represents a new herbaceous perennial grown for use as a landscape plant.

The Inventor discovered the new cultivar, 'Moonlight', in a container at his nursery in summer of 2007 in Lijnden, The Netherlands. 'Moonlight' originated as a naturally occurring branch mutation of *Disporum cantoniense* 'Aureovariegata' (not patented).

Asexual reproduction of the new cultivar was first accomplished by softwood cuttings in Lijnden, The Netherlands in summer of 2007 by the Inventor. Asexual reproduction has determined that characteristics of this cultivar are stable and are reproduced true to type in successive generations.

SUMMARY OF THE INVENTION

The following traits have been repeatedly observed and represent the characteristics of the new cultivar. These attributes in combination distinguish 'Moonlight' as unique from all other cultivars of *Disporum* known to the Inventor.

1. 'Moonlight' exhibits foliage that is green with silvery white variegation that palmately radiates from the base of the leaf blade.
2. 'Moonlight' exhibits fall foliage under cool temperatures in which the silvery-white variegation becomes heavily suffused with a purple-pink coloration.
3. 'Moonlight' exhibits arching branches.

'Moonlight' can be most closely compared to its parent plant, 'Aureovariegata'. 'Aureovariegata' differs from 'Moonlight' in having foliage that is inconspicuously variegated with green and pale greenish yellow leaves. 'Moonlight' can also be compared to 'Night Heron' (not patented) and 'Green Giant' (not patented). 'Night Heron' differs from 'Moonlight' in having a taller plant habit that is less arching and in having foliage that is purple-brown in spring and fading to green-purple in summer. 'Green Giant' differs from 'Moonlight' in being taller in height and in having green foliage with a purple tint on newly emerged leaves.

BRIEF DESCRIPTION OF THE DRAWING

The accompanying colored photographs illustrate the overall appearance and distinct characteristics of a one year-old plant of the new *Disporum* as grown outdoors in a garden in Lijnden, The Netherlands.

The photograph in FIG. 1 provides a view of the plant habit and foliage of 'Moonlight'.

Figure 1:
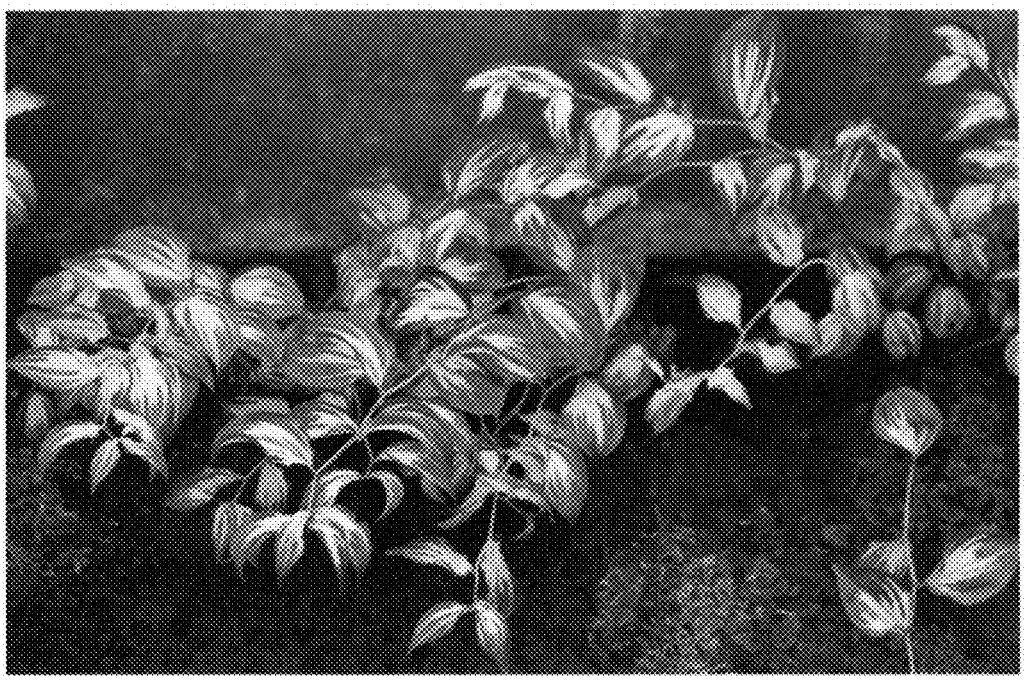
Figure 2:
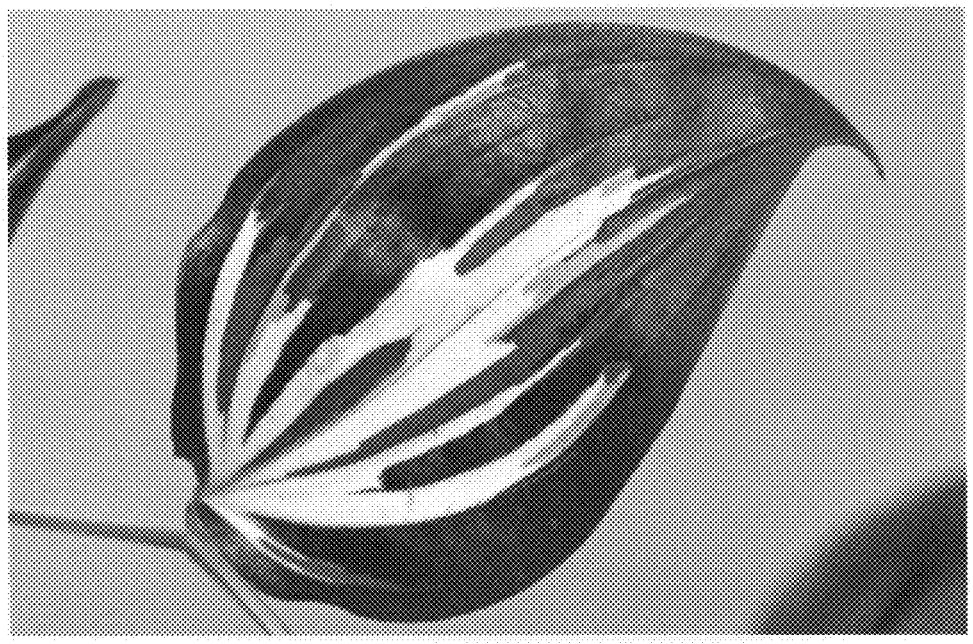

The photograph in FIG. 2 provides a close-up view of a leaf of 'Moonlight' in mid summer.

Figure 3:
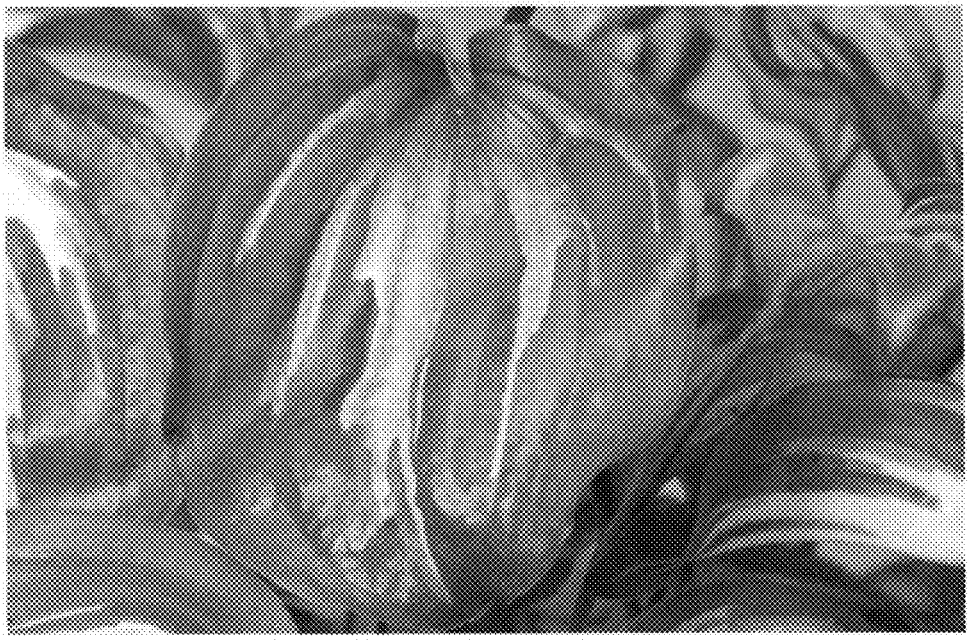

The photograph in FIG. 3 provides a close-up view of the leaf coloration in fall.

Figure 4:
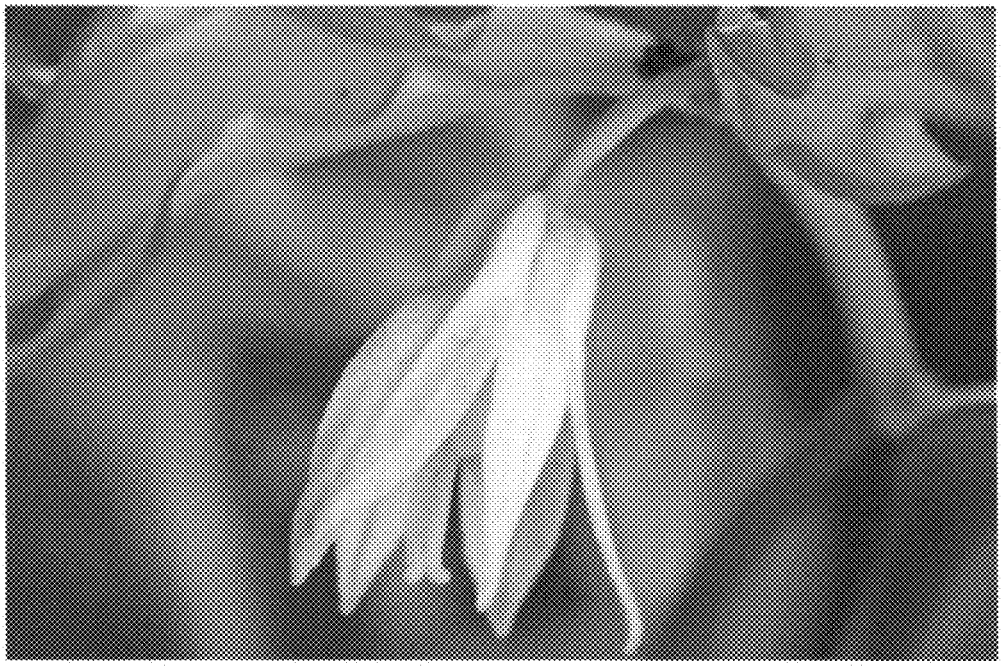

The photograph in FIG. 4 provides a close-up view of a flower of 'Moonlight'.

The colors in the photographs are as close as possible with the digital photography and printing techniques utilized and the color codes in the detailed botanical description accurately describe the new *Disporum.*

BOTANICAL DESCRIPTION OF THE PLANT

The following is a detailed description of one year-old plants of 'Moonlight' as field grown in Lijnden, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—April to May in The Netherlands.

*Plant habit.*—Herbaceous, clump-forming perennial, arching foliage.

*Height and spread.*—Reaches about 55 cm in height and width.

*Hardiness.*—At least to U.S.D.A. Zone 5.

*Diseases.*—Has been observed to be disease free, plants of the genus *Disporum* typically do not have disease problems.

*Root description.*—Fleshy roots, moderately dense, 156D in color.

*Propagation.*—Softwood cuttings.

*Growth rate.*—Moderately vigorous.

Stem description:

*Shape.*—Rounded to moderately angled.

*Stem color.*—144B, upper surface tinged with 177B, base a blend of 199A to 199B and N199C.

*Stem size.*—Average 32.1 cm in length and 2 mm in diameter.

*Stem surface.*—Moderately glossy.

*Branching.*—Basal branches only.

*Internode length.*—Average of 2.7 cm.

*Stem aspect.*—Held at about a 45° angle with end of stems curved downward at about a 30° angle.

Foliage description:

*Leaf shape.*—Ovate, slightly carinate with curved tip.

*Leaf division.*—Simple.

*Leaf base.*—Short attenuate.

*Leaf apex.*—Abruptly acuminate and curved.

*Leaf venation.*—Palmate, coloration on upper and lower surface match leaf color.

*Leaf margins.*—Entire.

*Leaf attachment.*—Petiolate.

*Leaf arrangement.*—Alternate.

*Leaf size.*—Average of 6.2 cm in length, 4.3 cm in width.

*Leaf quantity.*—An average of 11 per stem.

*Leaf surface.*—Glabrous, slightly carinate and moderately glossy on upper surface, glabrous, slightly carinate and slightly glossy on lower surface.

*Leaf color.*—Young upper surface; 143A to 143B with irregular palmate shaped variegation of 154D, mature upper surface; a color between 137A and N137A with areas of 144A with irregular palmate shaped variegation of 155A and a color between 154D and 157A, young lower surface; 143B with areas of 144A with irregular palmate shaped variegation of 154C and 154D, mature lower surface; 137B with areas of 144B with irregular palmate shaped variegation of 155A and a color between 154D and 157A, fall upper surface; whitish variegated area becomes heavily suffused with 186B, fall lower surface; whitish variegated area becomes heavily suffused with 186B.

*Durability to stress.*—Moderate to high.

*Petiole.*—An average of 3 mm in length and 2 mm in width, 145B in color, surface is glabrous.

Flower description:

*Inflorescence type.*—Terminal umbel.

*Lastingness of inflorescence.*—Determinate, blooms last approximately 10 days.

*Inflorescence size.*—About 1.9 cm in height and 1.6 cm in width.

*Flower fragrance* .—None.

*Flower aspect.*—Drooping.

*Flower type.*—Campanulate, partially closed.

*Flower size.*—About 1 cm in diameter and 1.5 cm in depth.

*Flower number.*—Average of 2 (varying from 1 to 3) per inflorescence.

*Tepals.*—Average of 6, un-fused, about 1.5 cm in length and 0.4 cm in width, acute apex, base un-fused, margins entire, smooth, dull and slightly velvety on upper and lower surface, color of upper surface when opening; 150D, color of lower surface when opening; 150D becoming darker at the tip; 150C, color of upper and lower surfaces when fully opened; between 150D and 154D.

*Flower buds.*—Ovate to oblong in shape, color 150D becoming 150C at the tip, an average of 7 mm in length and up to 4 mm in diameter.

*Peduncle.*—Average of 6 mm in length, about 8 mm in diameter, average angle to lateral stem is 35° (straight on top of lateral stem=0°), moderately strong and 148C to 148D in color.

*Pedicels.*—None, flowers are sessile to peduncle.

Reproductive organs:

*Gynoecium.*—3 pistils, style is 1 cm in length and 157D in color, stigma club-shaped and 150C in color, ovary is 145C in color.

*Androcoecium.*—6 stamens, filament is 4 mm in length and 144C in color, anther is oblong, 4 mm in length and 154C to 154D in color, pollen is low in quantity and 1C in color.

*Fruit and seed.*—No fruit or seed observed to date.

It is claimed:

1. A new and distinct cultivar of *Disporum* plant named 'Moonlight' substantially as herein illustrated and described.

* * * * *